United States Patent
Feng et al.

(10) Patent No.: US 9,289,622 B2
(45) Date of Patent: Mar. 22, 2016

(54) THERAPEUTIC LIGHT CONTROL SYSTEM

(75) Inventors: Xiao-fan Feng, Camas, WA (US); Jon M. Speigle, Vancouver, WA (US); M. Ibrahim Sezan, Camas, WA (US)

(73) Assignee: Sharp Laboratories of America, Inc., Camas, WA (US)

( * ) Notice: Subject to any disclaimer, the term of this patent is extended or adjusted under 35 U.S.C. 154(b) by 289 days.

(21) Appl. No.: 13/080,853

(22) Filed: Apr. 6, 2011

(65) Prior Publication Data

US 2012/0259392 A1 Oct. 11, 2012

(51) Int. Cl.
*A61N 5/06* (2006.01)

(52) U.S. Cl.
CPC ........ *A61N 5/0618* (2013.01); *A61N 2005/0628* (2013.01); *A61N 2005/0652* (2013.01); *A61N 2005/0663* (2013.01)

(58) Field of Classification Search
CPC ............ A61N 5/0618; A61N 2005/0663; G09G 3/3413; G09G 3/3426; G09G 2360/16
USPC .............................. 607/88–94; 600/300–301; 345/204–207, 690–696
See application file for complete search history.

(56) References Cited

U.S. PATENT DOCUMENTS

| | | | |
|---|---|---|---|
| 6,350,275 B1 | 2/2002 | Vreman et al. | |
| 6,554,439 B1 | 4/2003 | Teicher et al. | |
| 6,955,684 B2 | 10/2005 | Savage, Jr. et al. | |
| 7,679,281 B2 | 3/2010 | Kim et al. | |
| 2003/0069616 A1 | 4/2003 | Skene et al. | |
| 2006/0215388 A1* | 9/2006 | Hamada | 362/29 |
| 2008/0094541 A1* | 4/2008 | Ma et al. | 349/69 |
| 2008/0219013 A1 | 9/2008 | Budinger et al. | |
| 2008/0275533 A1 | 11/2008 | Powell | |
| 2009/0051642 A1* | 2/2009 | Huang et al. | 345/102 |
| 2009/0240311 A1* | 9/2009 | Andersen | 607/90 |
| 2009/0281604 A1* | 11/2009 | De Boer et al. | 607/88 |
| 2009/0326616 A1* | 12/2009 | Aarts et al. | 607/88 |
| 2010/0060195 A1 | 3/2010 | Tsuboi et al. | |
| 2010/0174345 A1* | 7/2010 | Ashdown | 607/88 |

(Continued)

FOREIGN PATENT DOCUMENTS

JP 2009-011582 A 1/2009

OTHER PUBLICATIONS

Stefani et al., Evaluation of Human Reactions on Displays with LED Backlight and a Technical Concept of a Circadian Effective Display, SID 10 Digest, ISSN 0097-966X/10/4102-1120, 2010, 4 pgs.

(Continued)

*Primary Examiner* — Lynsey Crandall
*Assistant Examiner* — Nathan J Jenness
(74) *Attorney, Agent, or Firm* — Chernoff Vilhauer McClung & Stenzel, LLP (57) ABSTRACT

A system for influencing a state of a user includes a display with a light source for emitting light influencing the state of the user. A light controller selectively controls the emission of the light including at least one of; (1) the spectrum of the light; (2) the duration of the light; 3) the distribution of the light; (4) the intensity of the light; and (5) the timing of the light. An analysis engine capable of providing a signal to the light controller indicating a desired emission of the light based upon selectively illuminating one or more of a plurality of different blue light sources, each of which having a different peak spectrum.

15 Claims, 8 Drawing Sheets

(56) References Cited

U.S. PATENT DOCUMENTS

2011/0144451 A1* 6/2011 Robertson .................... 600/300
2012/0101554 A1* 4/2012 Feather et al. .................. 607/88

OTHER PUBLICATIONS

Rea et al., Circadian light, Journal of Circadian Rhythms 2010 8:2, 10 pgs.

Rea et al., The potential of outdoor lighting for stimulating the human circadian system, Alliance for Solid-State Illumination Systems and Technologies (ASSIST), May 13, 2010, 11 pgs.

Figueiro et al., Developing Architectural Lighting Designs to Improve the Health and Well-Being of Older Adults, AIA report on University Research, vol. 3, 2005, 26 pgs.

International Search Report, mailed Jul. 17, 2012, PCT International Application No. PCT/JP2012/060092, Sharp Kabushiki Kaisha, 6 pgs.

\* cited by examiner

FIG. 1  LED CEILING LIGHTS

FIG. 2

FIG. 3 ALGORITHM TO DERIVE CIRCADIAN MODULATION-BASED ENVIRONMENT, TIME, AND PERSONAL PREFERENCE

FIG. 6 SYSTEM BLOCK DIAGRAM

FIG. 7 COLOR MANAGEMENT TO IMPROVE RENDERED IMAGE

FIG. 8 AREA ACTIVE LED DRIVING FOR CIRCADIAN RHYTHM WIDE COLOR GAMUT

THERAPEUTIC LIGHT CONTROL SYSTEM

CROSS-REFERENCE TO RELATED APPLICATIONS

Not applicable.

BACKGROUND OF THE INVENTION

The present invention relates generally to a therapeutic light control system.

The biological circadian rhythm in humans control important processes, such as the daily cycle of waking and sleeping. This biological rhythm tends to align its cycle to the external environment, such as the exposure of light modifying the hormone melatonin levels, which are associated with sleep. The melatonin synthesis is reduced when light impacts the retina of the eye. It may be desirable to modify the circadian rhythm to increase the well being of the person.

Aarts et al., U.S. Patent Application Publication 2009/0326616 disclose a system that influences a photobiological state of a person. The system includes a light source, a sensor that senses a first biophysical parameter of a person that is sent to a control circuit which sends a control signal to the light source so as to generate a predetermined photobiological state. The control signal provided by the control circuit is based upon the first biophysical parameter and another parameter, such as a biophysical parameter sensed at a different time.

Figure 1:
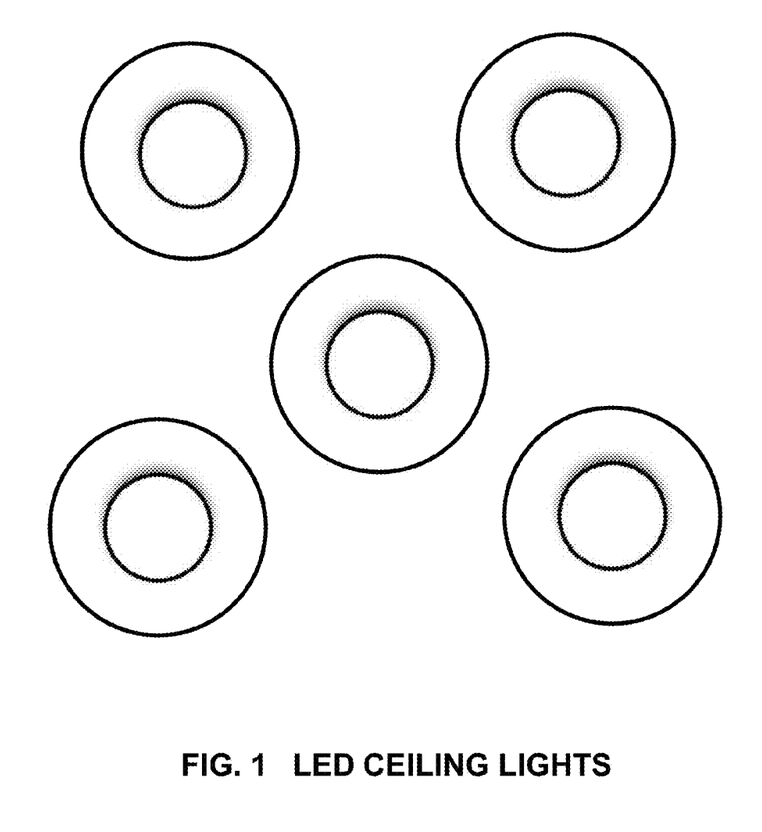
FIG. 1 illustrates LED based ceiling lights.

Referring to FIG. 1, an exemplary LED based ceiling light allows the use of a remote controller to change the color of a white light with an adjustable color function and to adjust the brightness with the dimmer function. These functions combine to offer 110 different levels of color and brightness that match the mood or time of day. These lights also feature an eco-light rhythm function, a lighting program that automatically adjusts the color and brightness throughout the day.

The foregoing and other objectives, features, and advantages of the invention will be more readily understood upon consideration of the following detailed description of the invention, taken in conjunction with the accompanying drawings.

DETAILED DESCRIPTION OF PREFERRED EMBODIMENT

While a light system provides wellness benefits to a user, different users tend to have different responses to the application of light. With different users having different responses to the application of light, it is desirable to include a feedback to the system so that the system may be suitably tuned to the particular user's characteristics. While many users will tend to have similar characteristics, most users will have somewhat different responses to the application of light for therapeutic and wellness benefits. With a suitable application of light, selected for the particular user based upon their individual characteristics, the user may achieve the improved health and wellness benefits.

By way of example, suitable exposure to light may provide responses that are shorter term (such as 0-3 hours of exposure) which are generally psychological in nature. For example, the application of an appropriate amount of soothing lights in a proper manner may calm the user and reduce their heart rate. By way of example, suitable exposure to light may provide responses that are longer term (such as several hours to days) which is primarily circadian in nature as controlled by melatonin levels. By way of example, suitable exposure to light may help manage sleep disorders, child hyperactivity learning, elderly safety, metal state, and concentration.

Figure 2:
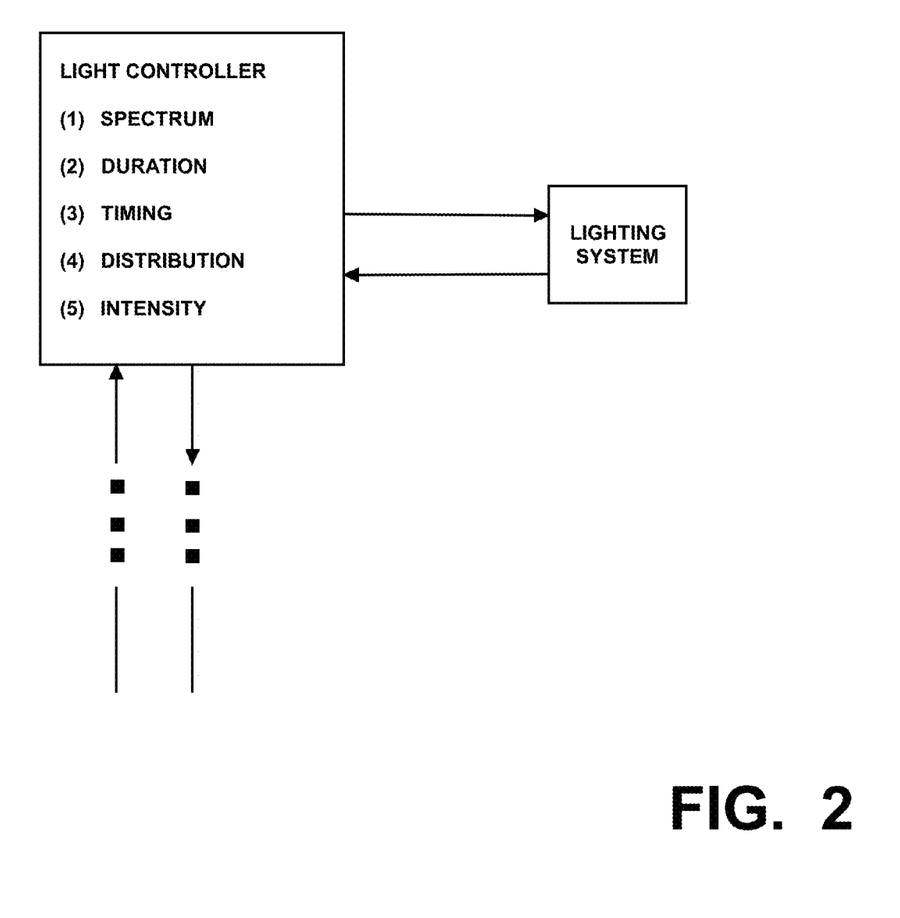
FIG. 2 illustrates a light controller and lighting system.

Referring to FIG. 2, a lighting system may be controlled by a light controller to manage a number of different attributes, each of which may individually or collectively contribute to the wellness and health of a user. Many users spend significant amounts of time in front of displays, such as televisions, desktop monitors, and mobile devices with integrated displays. These displays may be used as a light source to modify the viewer's biological circadian rhythm. The screen on such displays typically has multiple separate spectrums provided by multiple light sources, such as different light emitting diodes. The lighting system is preferably capable of generating light in the spectrum range of ~420 nm to ~500 nm especially suitable for circadian system stimulation, although any spectrum may be used. A first aspect of the lighting system may be the color spectrum of the lights. For example, the lighting system may have multi-colored lights which may be selected to provide desired color or colors to the user. For example, the lighting system may provide a selected color spectrum to the user among a set of different selectable color spectrums including different color temperatures, i.e., warm or cold light. For example, the color spectrum may be modulated or otherwise temporally varied. A second aspect of the lighting system may be the duration of illumination of the lights. For example, the lighting system may provide illumination for one or more selectable durations to the user. A third aspect of the light system may be spatial distributions or positions of one or more of the lights within the display. For example, the lighting system may have one or more one dimensional light arrangements or one or more two dimensional light arrangement, where selected lights are illuminated. For example, the lighting system may have a plurality of light sources (or otherwise the distribution of illumination from a light source) that may be spatially and/or temporally selectable. A fourth aspect of the light system may be the brightness of one or more of the lights. For example, the lighting system may selectively provide a low illumination to the user, a medium illumination to the user, and/or a high illumination to the user in a manner to contribute to the wellness and the health of the user. For example, the lighting system may selectively have different brightness for different light sources illuminating the user. A fifth aspect of the light system may be the timing of the light or lights. For example, one or more selected lights may be turned on during different parts of the day in different manners.

By selectively modifying one or more of these five different lighting attributes, various wellness and health attributes for the user may be modified. In particular, these modifications should be based upon the particular user so that the most effective wellness and heath benefits may be achieved. By way of example, suitable modification of one or more of these lighting attributes may manage sleep disorders, child hyperactivity learning disorders, elderly safety (e.g., fall avoidance), mental state, and concentration.

Figure 3:
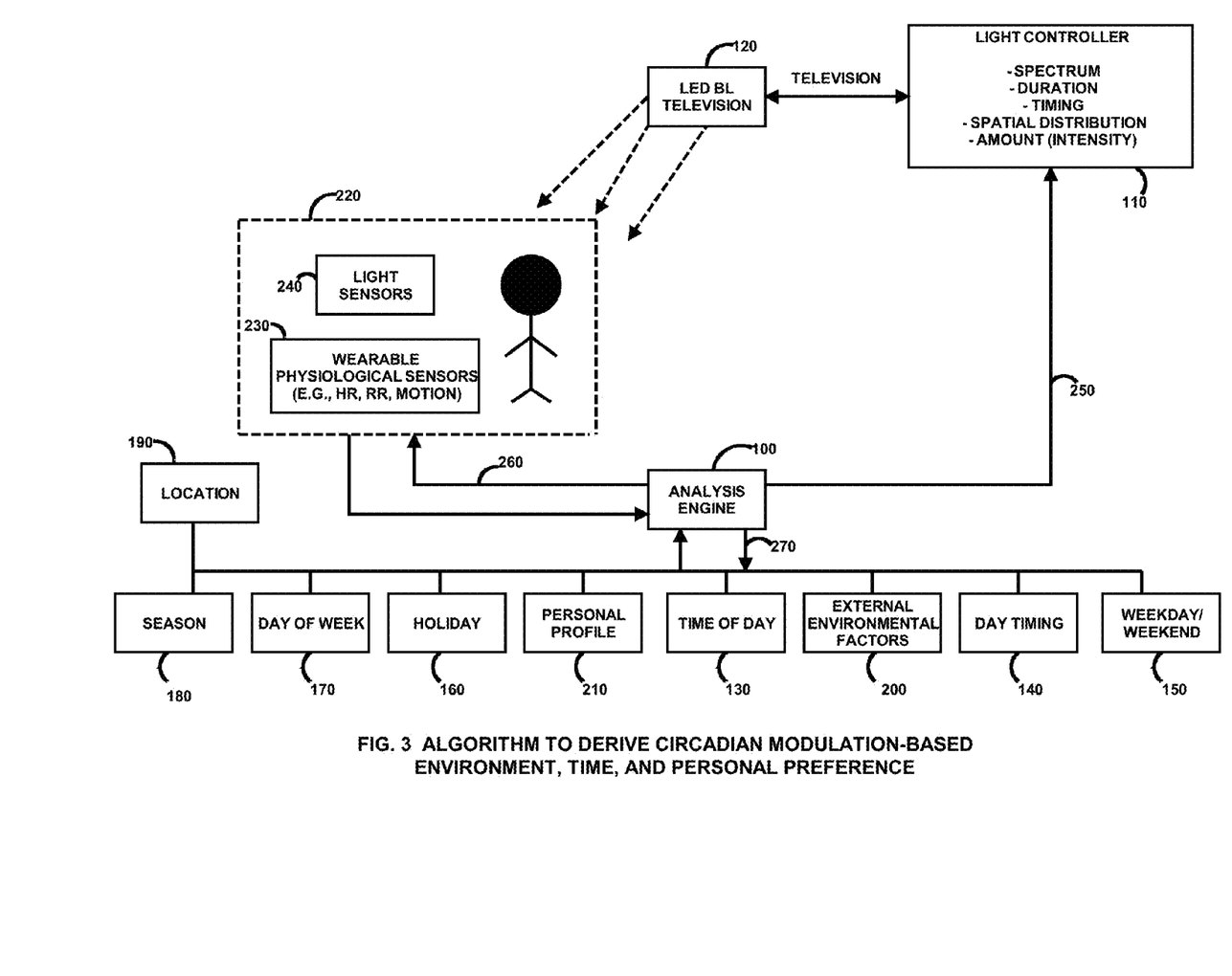
FIG. 3 illustrates a light control system.

Referring to FIG. 3, an analysis engine 100 may be used to selectively control a light controller 110 interconnected to a display 120. The analysis engine 100 may be operating on a local computer, a service on the Internet, or operating on a cloud computing platform, or otherwise. In some cases, a service provider may be provided to the user to which they may subscribe that provides suitable health services, customizable to the user. The service may be a subscription service to which the user subscribes. The light controller and analysis engine may be separate, or included as separate (or the same) processes on the same device. Also, the different components of the system may be interconnected using any suitable technique, such as wired or wireless communication. The analysis engine 100 may receive input regarding the time of day. The time of day information may be any suitable time based information, such as for example, (1) the current time of the day 130; (2) morning, afternoon, evening, or night 140; (3) a weekday or a weekend 150; (4) a holiday 160; (5) a particular day of the week 170; and/or (6) a season of the year 180. For example, the user may have different requirements in the evening versus the morning. For example, the user may have different requirements during the work week rather than the weekend. For example, a holiday may be a stressful time for the user and thus have different requirements than a non-holiday. For example, a user may have different requirements during the winter than the summer.

The analysis engine may also receive input regarding the user's general physical location 190. For example, a user in Alaska may have different requirements than a user in Colorado, which may likewise be different than the requirements for a user in Hawaii. In addition, the combination of the user's location together with the time of year may have result in different requirements. For example, a user in Alaska during the winter may have different requirements than either a user in Hawaii during the winter or a user in Alaska during the summer. For example, a user being in their home or at the office may result in different requirements.

The analysis engine may also receive environmental factors 200 regarding the user's current environment. Such environmental factors may include, for example, the current weather forecast; whether it is raining; whether it is foggy; whether it is sunny; whether it is overcast; whether it is hailing; whether it is lightening; whether it is flooding; whether it is cloudy; the current temperature; the anticipated temperature; the barometric pressure; and trends with all of the above. The environmental factors may likewise include current social conditions.

The analysis engine may also receive a personal profile 210 of the user. The personal profile may include information particularized to the user. Some of this particular information may include, for example, whether the user is a morning person or an evening person. The information may include an ophthalmologic characterization of the user, which is especially useful when the lighting system administers light using goggles worn close to the user's eyes. The profile may be specific to a particular user, a particular family, a group of people, or otherwise one or more users. The analysis engine may likewise base its processing on more than one profile, such as an average of a pair of profiles. In addition, the profile or profiles to be used by the analysis engine may be selected by a user or automatically selected by the system or otherwise selected based upon other input. Also, the profile may include health information for the user.

In many cases, users do not have the desire or motivation to manually create a profile. In this case, the user may link their profile to a social network account, such as for example, a Facebook account, a Twitter account, or a MySpace account. The analysis engine retrieves personal information from the social networking account, such as, relationship status, birthday, hometown name, hometown location, sex, employer, college, high school, interests, mood, political views, religious views, activities, interests, music, books, movies, television, and/or occupation. In addition, the user may enter information about their current and/or previous status into the social networking service that may be indicative of their state of mind or otherwise. Since a user tends to have friends, acquaintances, or others linked to their social networking account that are similar to themselves, similar information from another's account may be likewise used by the analysis engine. In addition, the personal profile may include a medical profile of the user, or otherwise the personal profile may be linked to an account that includes medical information, preferably medical information that is otherwise periodically updated. Moreover, some of the information in the user profile may be provided by answers to a set of questions. Personal profile may contain information about the mental state of the individual where such state is determined by the answers that the individual provides to a set of questions indicative of individual's focus and alertness. These may include gender, age, activity and/or other profile information.

The data obtained or otherwise determined as a result of the therapy, together with the results of the therapy, may be provided to the user's medical provider so that they can monitor the therapy. In general, the analysis engine may receive information from a variety of different sources, and may likewise provide information to the sources, as desired.

In some cases, the user's profile may be periodically synchronized from the user's mobile device. By using wireless, Bluetooth, or other communication techniques, the user's mobile device may provide personal information to the analysis engine about the user.

In addition, sensors 220 associated with the user may likewise provide data to the analysis engine. The sensors may include physiological sensors 230 and light sensitive sensors 240 in the environment of the user. Preferably, the light sensitive sensors and the physiological sensors are worn by the user. The physiological sensors may include, for example, heart rate sensors, time sensors, date sensors, location base sensor, acoustic sensor, body temperature sensor, respiration rate sensor, and/or motion sensor. The physiological sensor information accordingly provides information regarding the user's body. For example, if the user's heart rate is elevated then the analysis engine may be used to provide a light signal to reduce the heart rate. Likewise, the analysis engine may use the other information to provide health benefits. The light sensitive sensors, may be for example, a daysimeter device or a camera type sensor.

In some situations, the level or amount of exposure of light to a user in general, or a particular user, may be higher than a suitable level. In many cases, excessive exposure to light may in fact decrease the user's heath. In other cases, a sensor may sense the light exposure level to an individual's retina, and thus check and confirm that safety standards prevent toxicity by controlling light dosage. Accordingly, the analysis engine may use the light sensing information to determine safe lighting levels.

The system may further operate in a closed-loop configuration, if desired. The analysis engine while receiving information from many sources, can likewise provide control or feedback signals 250 to the lighting controller, and control or feedback signals to the physiological or light sensors 260 and sources 270 of data. For example, the analysis engine could provide feedback for the configuration of the sensors so that they acquire data in a more suitable manner or other configuration data. For example, the analysis engine could provide feedback for goggles worn by the user to control the amount of light received by the user. For example, the analysis engine may update the personal profile with other information. The analysis engine may likewise receive feedback from the light controller and light sensors so that it may monitor the light that is actually provided to the user. For example, the analysis engine may chose to invoke selected sensors to probe specific different characteristics, such as certain sensors placed at certain positions/locations in the house. In this manner, not all of the sensors need to be on at all times or otherwise configured in a particular. Also, the analysis engine also adjusts the sensitivity of individual sensors that are used to collect the data as needed to suitably control the lighting system.

In many cases, it is desirable to shift the primary used for the backlight from a backlight providing a first spectra peak, such as a blue spectra peak around 450 nm, to a backlight providing a second spectra peak, such as a blue spectra peak around 480 nm, or 420 nm. The different blue spectra peaks have a different effect on the melatonin suppression and can thus be effectively used by the system to selectively provide a more effective experience for the viewer.

Figure 4:
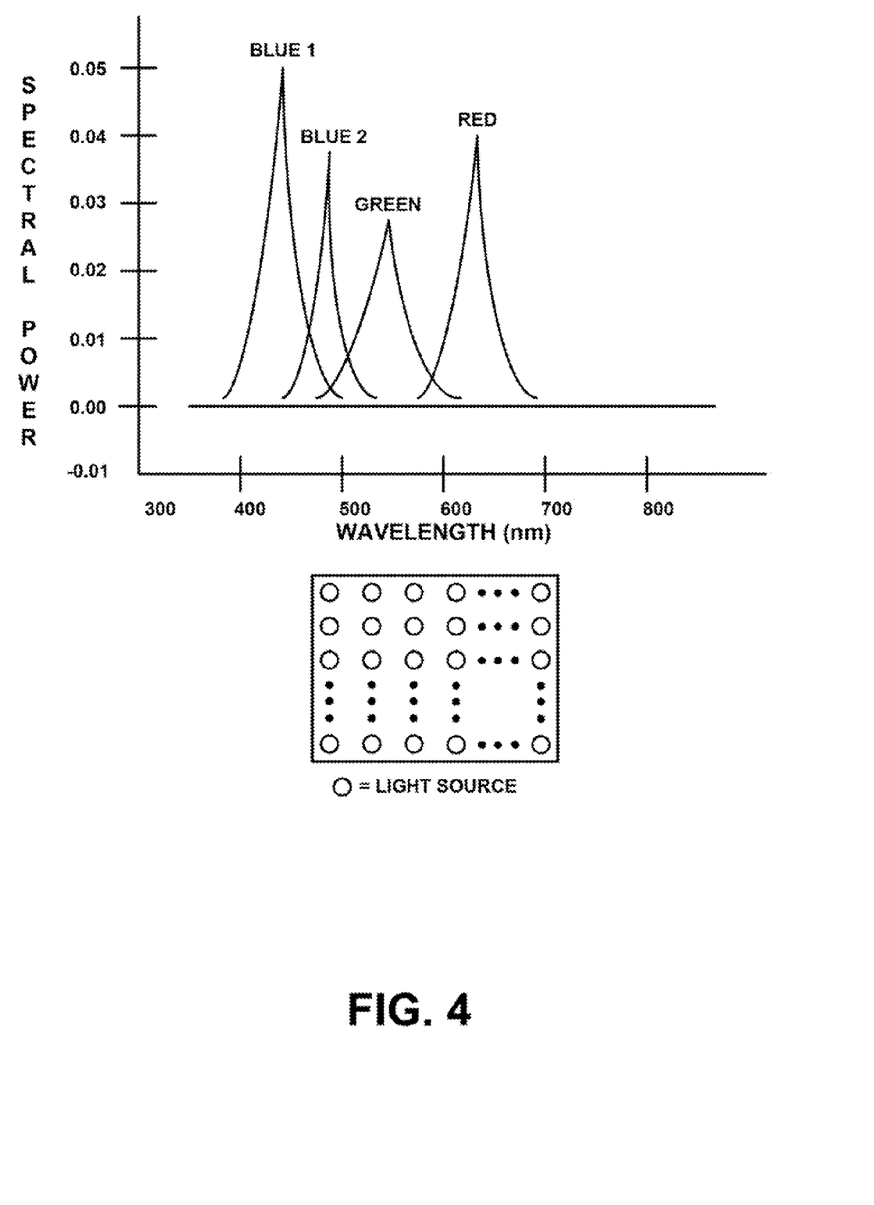
FIG. 4 illustrates a set of wavelength primaries.

Referring to FIG. 4, a backlight may include a plurality of backlight colors, at least two of which are the same general color. For example, the backlight may include a plurality of blue colors each having a different spectrum peak. The backlight spectra may include a first set of blue primaries (blue 1) together with a second set of blue primaries (blue 2), which shifts the blue to a wavelength that is away from circadian peak. Accordingly, the display may consist of a primary set (R,G,B1,B2) where the two short-wavelength blue primaries (B1 and B2) are suitable to achieve different balances between melatonin suppression and color gamut. The different blue primaries and/or the light resulting from them, may be spatially distributed across the display in any suitable manner.

Figure 5:
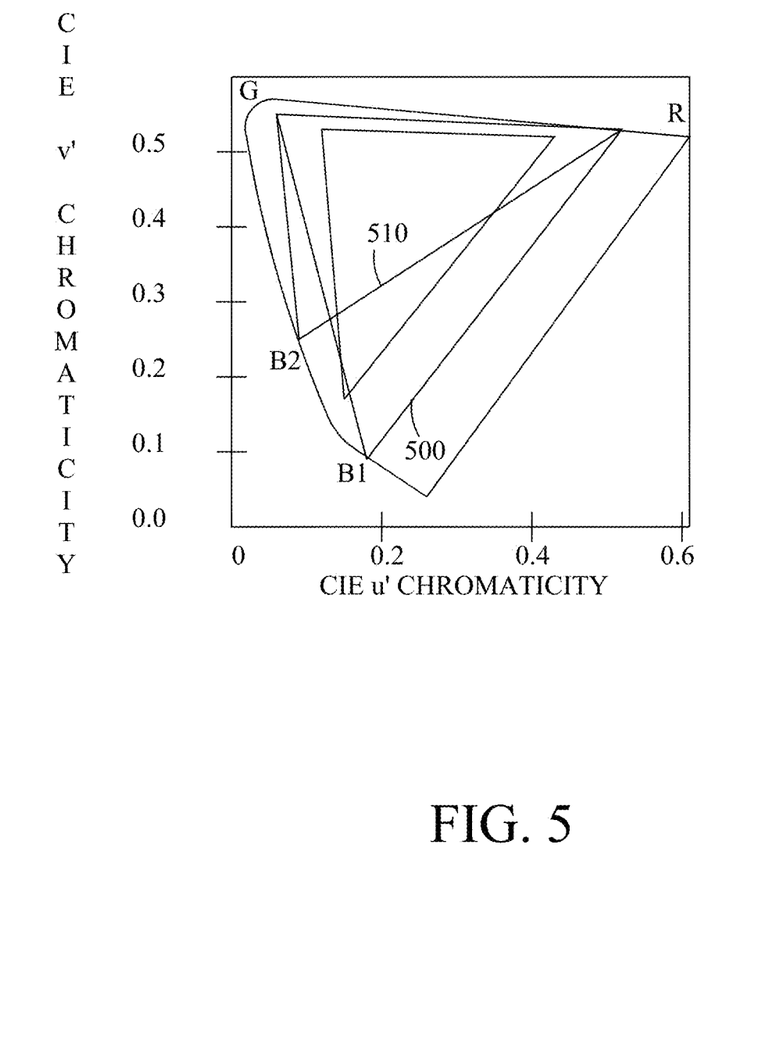
FIG. 5 illustrates CIE chromaticity with different backlight wavelengths.

Referring to FIG. 5, as a result of using different primaries, the range of chromaticity gamuts corresponding to the two exemplary primary sets (R,G,B1) 500 and (R,G,B2) 510 are different. The color gamut depends on the choice of the short-wavelength primary. Similarly, the melatonin suppression is modulated depending on which metamer (a*R,b*G,c*B1) or (d*R,e*G,f*B2) is used to determine a given CIE XYZ value. Generally, melatonin suppression is maximized when the peaks of the short-wavelength primary and melatonin suppression are aligned. But as the short- and middle-wavelength primary separation decreases, the color gamut decreases. An improved selection of primaries depends on this tradeoff, which is also affected by the choice of color rendering transform used to map an image onto the given set of primaries. With the two primary sets, the display can dynamically modulate between sets, or include both primaries, to achieve the desired circadian modulation. For a given pair of short-wavelength primaries, a weighted combination can also yield an effective color gamut intermediate to (R,G,B1) and (R,G,B2). Depending on the choices of B1 and B2, the maximal melatonin suppression response may occur for a mixture (when one short-wavelength primary does not align with the melatonin-suppression peak).

Figure 6:
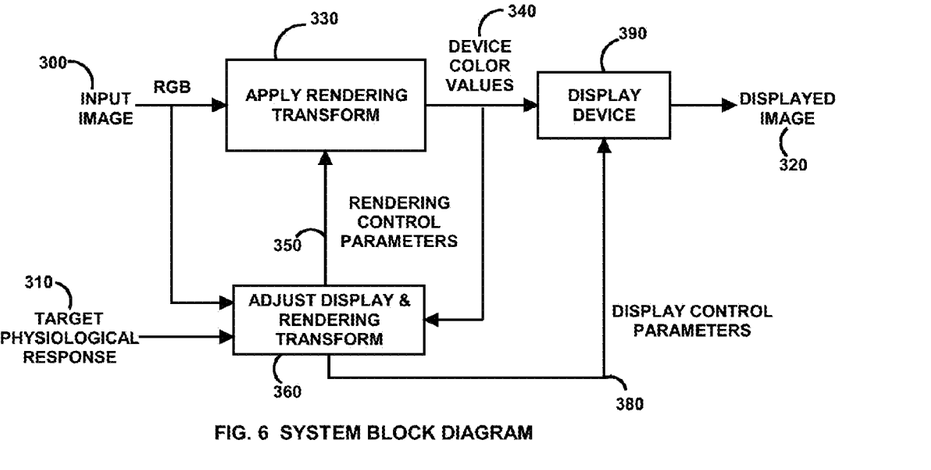
FIG. 6 illustrates a system block diagram.

The color gamut of the two primary sets shown in FIG. 5 may be compared to standard RGB primary (sRGB/Rec.709 RGB) 520, the color gamut of the primary with B2 is significantly different from the sRGB as depicted in CIE u'v' chromaticity diagram. Thus many colors may not be reproduced colorimetrically. Accordingly, it is desirable to modify the display technique to achieve both circadian modulation and to maintain good image quality. The technique may consist of one or more of the following:

(1) Rendering transform using whitepoint adaptation and XYZ-to-device mapping as illustrated in FIG. 6.

Figure 8:
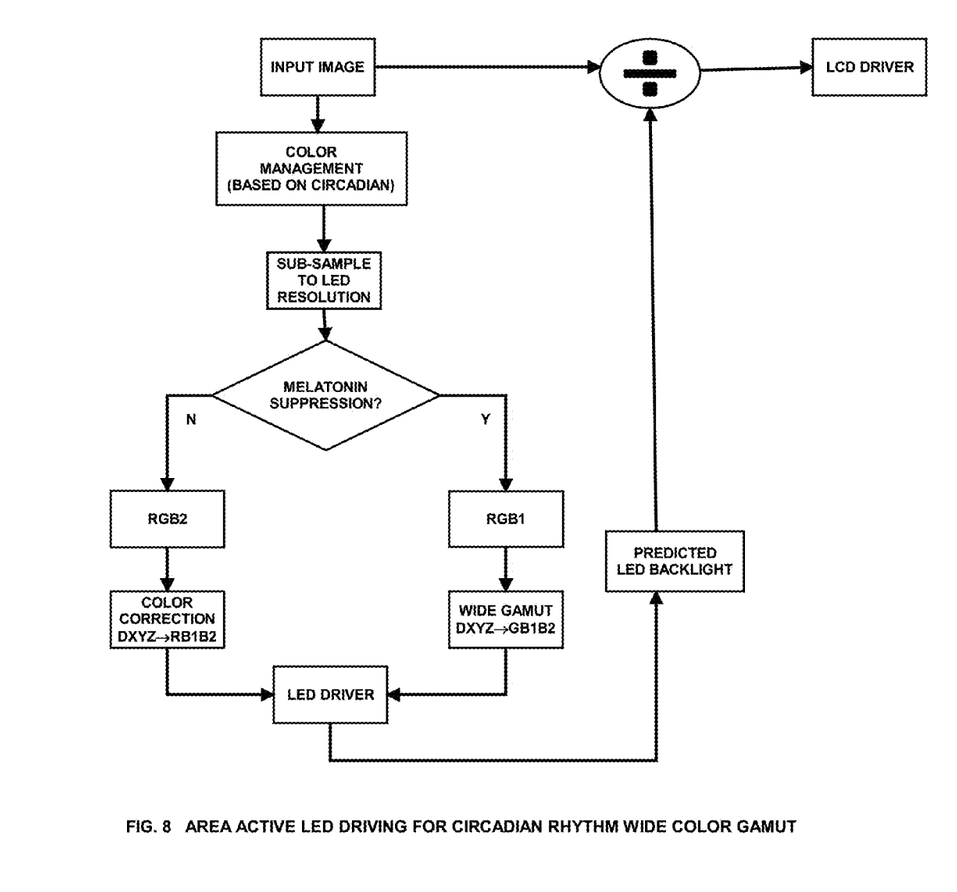
FIG. 8 illustrates an area active LED driving technique.

(2) Locally adaptive LED driving to select color metamers (e.g., between alternative short-wavelength primaries B1 and B2, and primary sets [R,G,B1] and R,G,B2]) that achieve the desired circadian modulation and color reproduction as illustrated in FIG. 8.

(3) Multi-primary rendering for a wide color gamut.

An exemplary technique is shown in FIG. 6. The inputs include an input image 300 and a target physiological response 310. The result of the technique is an adjusted display state of a displayed image 320 which approximates the target physiological response 310 while maintaining sufficient image quality. A rendering transform 330 converts the input image 300 to device color values 340 based upon rendering control parameters 350. The rendering control parameters 350 from an adjust display and rendering transform 360 may be selected based on the input image 300, estimated device color values 340 (dependent on the rendering and display settings), and the target physiological response 310. The rendering transform 330 can include elements for white point adjustment, color adaptation, colorimetric rendering, and/or gamut mapping. The rendering transform may also be dependent on the selection of the display device primary set and the spectral characteristics of the primary set. The display device 390 may be based upon the device color values 340 and display control parameters 380 provided for displayed image 320.

Figure 7:
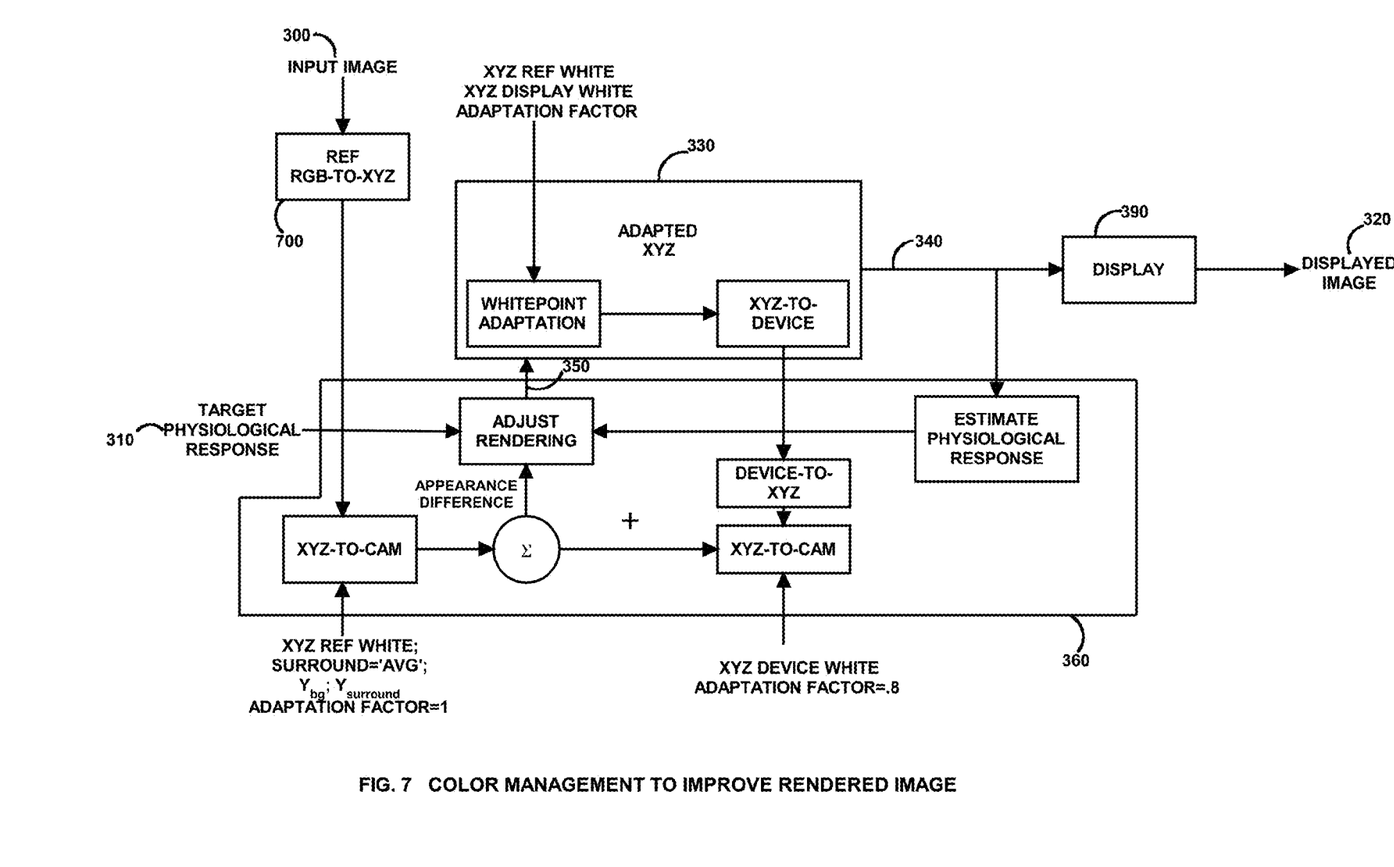
FIG. 7 illustrates a color management technique for rendering an image.

A more detailed diagram is shown in FIG. 7. The input image 300 may be represented as CIE XYZ 700 and further modified using a color appearance model (CAM) 710. Rendering of the input image 300 to device color values 340 may involve color adaptation and a device-independent color-space to device color mapping. The rendering parameters and display settings may be adjusted based on color appearance and physiological difference signals. The physiological response is estimated given the displayed image, knowledge of the selected display primaries, and a melatonin-suppression response model.

The melatonin-suppression model may be based on a spectral sensitivity template referred to as a nomogram; incorporate an estimated melanopsin pigment spectral sensitivity, rod input, and color opponent input based on the cone responses; or any other melatonin response model.

The device-independent to device-dependent color conversion may depend on the selected display primary set. The mapping achieves a balance between colorimetric rendering, gamut compression, and gamut mapping. The display may use any display technique, such as for example, field-sequential LED backlights and color-filter based displays with a global (0D), striped backlight (1D), or 2D backlit configurations. In each case, the display color rendering depends on the display primaries corresponding to each image position.

Referring to FIG. 8, another image processing approach uses a locally-adaptive color rendering to adjust the selected display primaries. This approach is especially suitable for 2D backlit displays which have a 2D array of backlight elements. Selection between display primaries is adaptively (locally) used to adjust the desired blue peak to modulate the circadian rhythm. To suppress the melatonin, B1 is used since its wavelength is near the peak of the melatonin suppression spectral sensitivity. On the other hand, to increase the melatonin level (e.g., when watching TV prior to sleep time), B2 is used more while B1 is added to the local areas where pure blue is desired for image quality. If melatonin suppression is needed (e.g., in the morning to increase alertness or to reinforce entrainment of the circadian cycle), B1 is used, and content is rendered using the RGB1 primary set as shown below.

$$\begin{pmatrix} R \\ G \\ B1 \end{pmatrix} = inv \begin{pmatrix} X_r & X_g & X_{b1} \\ Y_r & Y_g & Y_{b1} \\ Z_r & Z_g & Z_{b1} \end{pmatrix} \begin{pmatrix} X \\ Y \\ Z \end{pmatrix}$$

Where XYZ are the CIE tri-stimulus values, and the subscript denotes the primary color, e.g. $X_r$ is the red primary X value; and $Y_g$ is the green primary Y values. When colors are out of gamut in the cyan direction, the residue color (dXYZ) is rendered in the GB1B2 triangle as:

$$\begin{pmatrix} G \\ B1 \\ B2 \end{pmatrix} = inv \begin{pmatrix} X_g & X_{b1} & X_{b2} \\ Y_g & Y_{b1} & Y_{b2} \\ Z_g & Z_{b1} & Z_{b2} \end{pmatrix} \begin{pmatrix} dX \\ dY \\ dZ \end{pmatrix}$$

Where inv means matrix inversion. By using both B1 and B2, the system may achieve wide color gamut in the cyan direction.

When melatonin suppression is not desired (such as when watching TV in the evening), primary B2 is used as much as possible to reduce melatonin suppression. When the primary set is (R,G,B2), the rendering technique renders the image in the RGB2 triangle first as:

$$\begin{pmatrix} R \\ G \\ B2 \end{pmatrix} = inv \begin{pmatrix} X_r & X_g & X_{b2} \\ Y_r & Y_g & Y_{b2} \\ Z_r & Z_g & Z_{b2} \end{pmatrix} \begin{pmatrix} X \\ Y \\ Z \end{pmatrix}$$

If some colors are out gamut, the residue XYZ (dXYZ) is rendered in the RB1B2 triangle as:

$$\begin{pmatrix} R \\ B1 \\ B2 \end{pmatrix} = inv \begin{pmatrix} X_r & X_{b1} & X_{b2} \\ Y_r & Y_{b1} & Y_{b2} \\ Z_r & Z_{b1} & Z_{b2} \end{pmatrix} \begin{pmatrix} dX \\ dY \\ dZ \end{pmatrix}$$

Thus, the combination of R, G, B1, and B2 can effectively modulate the circadian rhythm and increase the color gamut of the display.

Similarly, it is possible to continuously vary the short-wavelength primary by using a weighted combination of the alternative short-wavelength primaries. For a global backlit system the CIE XYZ values of the short-wavelength primary are computed for the primary spectral weighting:

$xyz = w1*B1(\square) + w2*B2(\square)$ where w1=[0,1] and w2=[0,1].

Control of the weighting is based on the desired melatonin suppression and image characteristics.

In a 1D or 2D backlit system, where spatially-varying values are used for B1 and B2, the short wavelength primary XYZ values are computed given knowledge of the position-dependent LED values and estimates of the LED element point-spread functions.

Alternative color management methods can be used for the XYZ-to-device operation. Traditional color rendering operations include gamut compression and gamut mapping. Implementation can be algorithmic or precomputed and stored as 3D LUTs. Advantages of these methods include control of how within-gamut colors are compressed to make room for mapping of out-of-gamut colors, as well as gamut expansion when the source gamut is smaller than the destination gamut at some hues. Gamut mapping algorithms also control the tradeoff between hue, lightness and saturation preservation in the gamut mapped content. Image-dependent algorithms have the further advantage that gamut compression is avoided for images not containing out-of-gamut colors. Spatially-varying methods tradeoff luminance and chromatic color detail preservation in out-of-gamut regions.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

We claim:

1. A system for influencing a state of a user, said system comprising:
   (a) a display with a light source for emitting light suitable to use an input image to render an output image on said display, and to influence the state of the user;
   (b) a light controller selectively controlling said emission of said light to render said output image;
   (c) an analysis engine indicating a desired emission of said light characterized by selective illumination of a plurality of blue light sources having different respective spectral characteristics, wherein a first one of said blue light sources emits primarily blue light having a peak spectrum at a first wavelength, wherein a second one of said blue light sources emits primarily blue light having a peak spectrum at a second wavelength so as to increase melatonin levels in a viewer, wherein said first wavelength is different than said second wavelength, and where said analysis engine analyzes said input image to determine a relative mixture of light emitted by said first one of said blue light sources and light emitted by said second one of said blue light sources, with respect to each other, to produce said output image, where said relative mixture varies spatially over the output image and where the analysis of said input image is used by said analysis engine to determine a spatial variance of said relative mixture such that more light from said first one of said blue light sources is added to local areas of said image prioritized by said analysis engine for image quality.

2. The system of claim 1 wherein said different blue light sources are spatially distributed across a majority of said light source.

3. The system of claim 1 wherein one of said blue light sources is selected for illumination to reduce melatonin production in a viewer.

4. The system of claim 1 wherein one of said blue light sources is selected to increase melatonin production in a viewer.

5. The system of claim 1 wherein said mixture of said plurality of different blue light sources is selected based upon a desired change in melatonin production in a viewer.

6. The system of claim 1 wherein said light controller is modulated based upon at least one of (a) a profile of said user and (b) an identification of a particular said user.

7. The system of claim 6 further comprising said analysis engine obtaining information from said profile from a mobile device.

8. The system of claim 1 further comprising said analysis engine obtaining information regarding a time of day.

9. The system of claim 1 further comprising said analysis engine obtaining information regarding a physical location of said user.

10. The system of claim 1 further comprising said analysis engine obtaining information regarding environmental factors of said user.

11. The system of claim 1 further comprising said analysis engine obtaining information regarding social networking.

12. The system of claim 1 further comprising said analysis engine obtaining information regarding medical information.

13. The system of claim 1 further comprising said analysis engine obtaining information from a light sensor associated with said user.

14. The system of claim 1 further comprising said analysis engine obtaining information from a physiological sensor associated with said user.

15. The system of claim 1 further comprising limiting exposure to said light based upon a safety factor.

* * * * *